United States Patent [19]

Hellstrand et al.

[11] Patent Number: 5,348,739

[45] Date of Patent: Sep. 20, 1994

[54] COMBINED ANTI-TUMOR THERAPY WITH INTERLEUKIN-2 AND HISTAMINE, ANALOGS THEREOF OR H$_2$-RECEPTOR AGONISTS

[75] Inventors: Jan U. K. Hellstrand, Molndal; Svante H. Hermodsson, Bergsbdgaban, both of Sweden

[73] Assignee: Suntello, Inc., San Diego, Calif.

[21] Appl. No.: 843,052

[22] Filed: Mar. 2, 1992

Related U.S. Application Data

[63] Continuation-in-part of Ser. No. 409,357, Sep. 19, 1989, abandoned.

[51] Int. Cl.$^5$ .................. A61K 45/05; C07K 3/00
[52] U.S. Cl. .................. 424/85.2; 424/85.1; 530/351; 514/21; 514/885; 514/889; 514/400; 548/335.5
[58] Field of Search .................. 424/85.2, 85.1; 530/351; 514/21, 885, 889; 548/344

[56] References Cited

PUBLICATIONS

Osband et al, *The Lancet* vol. 1, No. 8221, pp. 636–638, Mar. 21, 1981.
Burtin et al, *Cancer Letters*, vol. 12, No. 3, pp. 195–201, Apr. 1981.
Lotze et al, *Interleukin 2*, ed. K. A. Smith, Academic Press Inc., San Diego, Calif., pp. 237–245, 1988.
Rosenberg, *Annals of Surgery*, vol. 208, No. 2, pp. 121–135, Aug. 1988.
Philips, et al. J. Exp. Med., vol. 170, pp. 291–296 (1989).
Schleimer, et al. J. Immunol., vol. 143, pp. 1310–1317 (Aug. 1989).
Alam, et al. J. Immunol., vol. 142, No. 10, pp. 3431–3435 (1989).
Richtsmeier, et al. Anol. Otol. Rhinol. Laryngol., vol. 96, No. 5, pp. 569–572 (1987).
Dohlsten, et al. Cellular Immunol., vol. 101, No. 2, pp. 493–501 (1986).
Nair, M. P. N. et al., J. Immunol. 136:2456 (1986).
Dempsey, R. A. et al., J. Immunol. 129:2504 (1982).
Segerson, T. P. et al. Science 238:75 (1987).
Hellstrand, K., et al., Int. Archs. Allergy Appl. Immun. 84:247–255 (1987).
Smith, K. A. Science 240:1169 (1988).
Rosenberg, S., Ann. Surgery 108:111 (1988).
Hanna, N. Biochim. Biophys. Acta 780:213 (1985).
Beer, D. J. et al., Adv. Immunol. 35:209 (1984).
Barna, B. P. et al., Oncology 40:43 (1983).
Lespinats, G. et al., Br. J. Cancer 50:545 (1984).
Nordlund J. J. et al., J. Invest. Dermatol 81:28 (1983).
Droege, W. et al., Chem Abstracts, vol. 104, No. 17, Apr. 28, 1986, Abstract 146898m.
Okamoto, H., "Possible Involvement of Adenosine 3'–5'–Cyclic Monophosphate . . . " Immunology, 70:186–190 (1990).

(List continued on next page.)

*Primary Examiner*—Michael G. Wityshyn
*Assistant Examiner*—Abdel A. Mohamed
*Attorney, Agent, or Firm*—Knobbe, Martens, Olson & Bear

[57] ABSTRACT

A method of inhibiting the development of malignant tumors and the formation of metastases of malignant tumor cells in a subject carrying the comprises administering to the subject IL-2 and an agent selected from the group consisting of histamine, a histamine structural analogs having H$_2$-receptor activities, an endogenous histamine releasing preparation, and a non-histamine derivative H$_2$-receptor agonist; the agent and the IL-2 being administered in amounts and for a time effective to attain the desired effect. A method of increasing the anti-tumor cell effect of IL-2 in a subject comprises co-administering to the subject IL-2 and an agent such as histamine, histamine structural analogs having H$_2$-receptor activities, endogenous histamine releasing preparations or H$_2$-receptor agonists, the agent and the IL-2 being administered in anti-tumor effective amounts and for a period of time effective to attain the desired effect.

23 Claims, 2 Drawing Sheets

OTHER PUBLICATIONS

Hellstrand, "Histamine $H_2$-Receptor Mediating Regulation of Human Natural Killer Cell Activity," J. Immunol, vol. 137, No. 2, pp. 656–660, Jul. 15, 1986.

Hellstrand, "Enhancement of Human NKCC by Serotonin," Cellular Immunol., vol. 127, pp. 199–214 (1990).

Hellstrand, "Role of Serotonin in the Regulation of Human Natural Killer Cell Cytotoxicity," J. Immunol., vol. 139, No. 2 pp. 869–875, published Aug. 1, 1987.

Hellstrand, "Monocyte Induced Down-Modulation of CD16 and CD56 Antigens on Human NK Cells and Its Regulation by Histamine $H_2$-Receptors," Cellular Immunol., vol. 138, pp. 44–54 (1991).

Dillman, et al., "Recombinant Interleukin-2 and Adoptive Immunotherapy Alternated With Dacarbazine Therapy in Melanoma: A National Biotherapy Study Group Trial," J. National Cancer Institute, 82(16):1345–1348, Aug. 15, 1990.

Hellstrand, "Cell-to-Cell Mediating Inhibition of NK Cell Proliferation by Monocytes and its Regulation by Histamine $H_2$-Receptors," Scand. J. Immunol., vol. 34, pp. 741–752 (1991).

Hellstrand, "Synergistic Activation of Human NKCC by Histamine and IL-2," Int. Arch. Allergy Appl. Immunol., vol. 92, pp. 379–389 (1990).

Hellstrand, "Role of Histamine in NK Cell-Mediated Resistance Against Tumor Cells," J. Immunol., vol. 145, No. 12, pp. 4365–4370, Dec. 15, 1990.

Hellstrand, et al., "Interleukin-2 Can Induce Suppression of Human Natural Killer Cell Cytotoxicity," Clin. Exp. Immunol., 77(3):410–416 (1989).

Hellstrand, "Monocyte Mediated Suppression of IL-2 Induced NK Cell Activation," Scand. J. Immunol., vol. 32, No. 2, pp. 183–192 (1990).

Hellstrand, "A Cell-to-Cell Mediated Interaction Involving Monocytes and Non-T/CD16=NK Cells is Required for Histamine $H_2$-Receptor Medicated NK Cell Activation," Scand. J. Immunol., vol. 31, pp. 631–644 (1990).

Hellstrand, BiogenicAmines in the Regulation of Human Natural Killer Cell Cytotoxicity (Thesis), Medi Press, Göteborg, Sweden, 1987.

Smith, "Histamine Type 2-Receptor Antagonists and Cancer Immunotherapy," Comprehensive Therapy, 16(1):8–13 (1990).

Schantz, et al., "A Phase II Study of Interleukin-2 and Interferon-Alpha in Head and Neck Cancer," Investigation New Drugs, 10:217–223 (1992).

Mavligit, et al., "Splenic Versus Hepatic Artery Infusion of Interleukin-2 in Patients with Liver Metastases," J. Clin. Oncol., 8(2):319–324 (Feb. 1990).

Krigel, et al., "Renal Cell Carcinoma: Treatment With Recombinant Interleukin-2 Plus Beta-Interferon," J. Clin. Oncol., 8(3):460–467 (Mar. 1990).

Dutcher, et al., "A Phase II Study of High-Dose Continuous Infusion Interleukin-2 With Lymphokine-Activated Killer Cells in Patients with Metastic Melanoma," J. Clin. Oncol., 9(4):641–648 (Apr. 1991).

Dillman, et al., "Continuous Interleukin-2 and Lymphokine-Activated Killer Cells for Advanced Cancer; A National Biotherapy Study Group Trial," J. Clin. Oncol., 9(7):1233–1240 (Jul. 1991).

Stoter, et al., "Sequential Administration of Recombinant Human Interleukin-2 and Dacarbazine in Metastic Melanoma: A Multicenter Phase II Study," J. Clin. Oncol., 9(9):1687–1691 (Sep. 1991).

Weiss, et al., "A Randomized Phase II Trial of Continuous Infusion Interleukin-2 or Bolus Injection Interleukin-2 Plus Lymphokine-Activated Killer Cells for Advanced Renal cell Carcinoma," J. Clin. Oncol., 10(2):275–281 (Feb. 1992).

Abrams, et al., "High-Dose Recombinant Interleukin-2 Alone: A Regimen with Limited Activity in the Treatment of Advanced Renal Cell Carcinoma," J. National Cancer Institute, 82(14):1202–1206 Jul. 18, 1990.

Hellstrand, "Serotonergic 5-HT1A Receptors Regulate a Cell Contact Mediated Interaction Between NK Cells and Monocytes," Scand. J. Immunol., vol. 37, pp. 7–18, published 1993.

Mertens, et al., "Sustained Indomethacin and Ranitidine with Intermittent continuous Infusion Interleukin-2 in Advanced Malignant Melanoma: A Phase II Study," J. Clinical Oncology, 5(2):107–113 (1993).

Mertens, et al., "Effect of Indomethacin Plus Ranitidine in Advanced Melanoma Patients on High-Dose Interleukin-2," Lancet, 340:397–398, Aug. 15, 1992.

Saarloos, et al., "Effects of Cancer Immunotherapy with Indomethacin and Interleukin-2 on Murine Hemo- (List continued on next page.)

OTHER PUBLICATIONS poietic Stemk Cells," Cancer Research, 52:6452–6462, Dec. 1, 1992.

Saarloos, et al., "Effects of Histamine Type-2 Receptor Antagonists on Indomethacin and IL-2 Immunotherapy of Metastasis," Clin. Exp. Metastasis, 11(3):275–283 (1993).

Khoo, et al., "Immunotherapy of Mammary Adenocarcinoma Metastases in C3H/HeN Mice with Chronic Administration of Cyclo-Oxygenase Inhibitors Alone or in Combination with IL-2," Clin. Exp. Metastasis, 10(4):239–252 (1992).

Sleijfer, et al., "Phase II Study of Subcutaneous Interleukin-2 in Unselected Patients With Advanced Renal Cell Cancer on an Outpatient Basis," J. Clin. Oncol., 10(7):1119–1123 (Jul. 1992).

Ilson, et al., "A Phase II Trial of Interleukin-2 and Interferon Alfa-2a in Patients with Advanced Renal Cell Carcinoma," J. Clin. Oncol., 10(7):1124–1130 (Jul. 1992).

Thompson, et al., "Prolonged Continuous Intravenous Infusion Interleukin-2 and Lymphokine-Activated Killer-Cell Therapy for Metastatic Renal Cell Carcinoma," J. Clin. Oncol., 10(6):960–968 (Jun. 1992).

Budd, et al., "Phase I Trial of High-Dose Bolus Interleukin-2 and Interferon Alfa-2a in Patients With Metastatic Malignancy," J. Clin. Oncol., 10(5):804–809 (May 1992).

Hallstrand, "Regulation of the NK Cell Response to IFN-$\alpha$by Biogenic Amines" J. Interferon Rsch., vol. 12, pp. 199–206 (1992).

COMBINED ANTI-TUMOR THERAPY WITH INTERLEUKIN-2 AND HISTAMINE, ANALOGS THEREOF OR H$_2$-RECEPTOR AGONISTS

This is a continuation-in-part of application Ser. No. 07/409,357 filed Sep. 19, 1989 now abandoned.

TECHNICAL FIELD

This invention relates to the field of anti-tumor therapy, and more particularly to the treatment of malignant tumors with interleukin-2 (IL-2). The improvement provided by the present method is the co-administration of the IL-2 with an agent such as histamine, histamine structural analogs having H$_2$-receptor activities, endogenous histamine releasing preparations, or non-histamine derivative H$_2$-receptor agonists. Unexpectedly potentiated effects are observed in the killing of tumor cells by components of the immune system and the prevention or inhibition of metastases of tumor cells.

BACKGROUND ART

Histamine has been shown to suppress a variety of immune effector mechanisms in vitro. This property of histamine is H$_2$-receptor associated. This effect has been described in the literature as being either directly or indirectly mediated. The direct effect is exerted via the cAMP-mediated suppression of immunocompetent cells. The indirect effect is mediated via the formation of histamine-induced suppressive proteins by suppressor T cells (see, Beer, D. J. et al, Adv. Immunol. 35:209 (1984)).

The concept that histamine may provide a suppressive signal for immune effector cells has also provided the background for other types of studies. One example is the testing of the potential anti-neoplastic effect of cimetidine and other H$_2$-receptor blockers, alone or in combination with other anti-neoplastic agents. Results of tests on the effects of these agents on tumor formation which have been conducted in rodents and humans are, however, conflicting. On one hand, the administration of H$_2$ blockers has been reported to suppress tumor development in rodents and human subjects (see, e.g., Osband, M. E. et al, Lancet 1(8221): 636 (1981). Other studies, on the other hand, report that the same treatment enhances tumor growth and even induces tumors (see, e.g., Barna, B. P. et al, Oncology 40:43 (1983)).

Histamine has also been shown to suppress rather than enhance the growth and occurrence of several types of tumors (see, e.g., Burtin, C. et al, Cancer Lett. 12:195 (1981)). The mechanism for the anti-tumor effects of histamine is not known but has been attributed to H$^1$ receptor activity (see, e.g., Lespinats, G. et al Br. J. Cancer 50:545 (1984)).

Again, contradictory data exist in this area as well. Histamine, for instance, has been reported to accelerate tumor growth in rodents (Nordlund J. J. et al J. Invest. Dermatol 81:28 (1983)).

Interleukin-2 (IL-2) is a lymphokine which has been ascribed a pivotal role in the expansion of T cells in response to antigen (Smith, K. A. Science 240:1169 (1988)). IL-2 has been shown to exert anti-tumor effects in rodents (see e.g., Lotze, M. T. et al, in "Interleukin 2", ed. K. A. Smith, Academic Press Inc., San Diego, Calif., p. 237 (1988); Rosenberg, S., Ann. Surgery 208:121 (1988)). IL-2 has also been shown to induce partial regression of established tumors in patients with different types of cancer (Rosenberg, S. A. Ann. Surgery 208:121 (1988)). The anti-tumor effect of IL-2 is potentiated when the compound is given together with autologous lymphocytes which have been cultured in vitro with IL-2 and subsequentially been reinfused to the patient (lymphokine-activated killer (LAK) cells) (Rosenberg, S. A., Ann. Surgery 208:121 (1988)). This effect is seen both in rodents and in humans. When used in human anti-cancer trials, IL-2 is usually given at very high doses to human tumor-bearing subjects and has been reported to induce serious side effects, including renal disturbances, anemia, reduced platelet counts, and cardiorespiratory effects. In several of these trials the H$_2$-receptor antagonist ranitidine was used to prevent IL-2 induced dyspepsia and nausea (Rosenberg, supra).

NK cells are considered to play an important role in a host's defenses against arising neoplasms as well as against metastases (Hanna, N., Sur. Synth. Pathol. Res. 2:68 (1983); Hanna, N. Biochim. Biophys. Acta 20 780:213 (1985)). Activation of NK cells, in turn, is known to increase a host's resistance against tumor cells (see, e.g., Lotze, M. T. et al., supra).

The following are individual in vitro effects of histamine and IL-2 on the regulation of human NK cells known at the time of this invention.

(1) Histamine augments human NK cell cytotoxicity (NKCC) via H$_2$-receptors

Histamine, at concentrations of $10^{-4}-10^6$ M, has been shown to strongly augment the NKCC of human mononuclear cells (MNC) against K562 leukemic cells. The effect is noted both when the effector cells used are unfractionated MNCs or cells enriched for large granular lymphocytes (LGL) by Percoll density gradient centrifugation. The NK-augmenting response to histamine is also mimicked by the H$_2$-receptor agonist dimaprit with similar potency and efficacy. Two structural analogs to dimaprit, nor-dimaprit and N-methyl-dimaprit, both lacking activities as H$_2$-receptors, proved to be ineffective under the same test conditions. The NK-augmenting effects of histamine and dimaprit were shown to be completely antagonized by the H$_2$-receptor antagonists ranitidine and cimetidine. The NK-augmenting effect of histamine was shown to require the presence of monocytes. In the absence of monocytes, histamine had no effect or weakly suppressed NKCC at the histamine concentrations mentioned. (Hellstrand, K., et al, J. Immunol. 137:656 (1986)).

(2) Histamine suppresses NK cell activity via T cells

In contrast to the above-mentioned NK cell activation induced by histamine in the presence of monocytes, histamine has been reported to suppress NKCC against K562 cells in the presence of T lymphocytes. Thus, in vitro treatment of human T cells with histamine ($10^{-3}-10^{-8}$ M) induces the production of a soluble factor, histamine-induced soluble suppressor factor (HISSF) that inhibited NK cell cytotoxicity. NK cells alone do not produce HISSF. Production of HISSF induced by histamine is blocked by cimetidine but not by an H$_1$-receptor antagonist. The inhibition of NK cell cytotoxicity by HISSF is reduced by the addition of IL-2 (6.4–64 U/ml) or interferon-$\alpha$ (500 U/ml) (Nair, M.P.N. et al., J. Immunol. 136:2456 (1986)). Further, it has been shown that the T-cell mediated suppressive effect of histamine on NK-cell related cytotoxicity is more pronounced in the presence of IL-2 (Welt, S. et al., Proc. Annu. Meet. Am. Soc. Clin. Oncol. 7:A632 (1988)).

(3) Enhancement Of NK Cell Cytotoxicity by IL-2.

IL-2 rapidly and effectively augments the cytotoxicity of isolated human NK cells in vitro over a broad range of concentrations. The effect has been described both with natural and recombinant forms of IL-2 (Dempsey, R. A., et al., J. Immunol. 129:2504 (1982); Phillips, J. H., et al., J. Exp. Med. 170:291 (1989)). The NK-augmenting effect of IL-2 is related to a cellular IL-2 receptor (IL-2R), p 75 (IL-2Rα) which is expressed on human NK cells (Siegel, J. P. Science 238:75 (1987); Phillips, J. H., et al., supra). The effect of IL-2 on NK cells is of relevance for the anti-tumor effect induced by this compound since depletion of NK cells from mice was reported eliminate anti-tumor effects induced by IL-2 treatment (Lotze, M. T., et al., supra).

In view of the high incidence of cancer in the human population and the at best partial success obtained at present with the different therapies in existence, there is still a need for further improved methods of treating tumors in humans.

Disclosure of the Invention

This invention relates to a method of inhibiting tumor growth and the formation of metastases of malignant tumor cells in a subject carrying the cells comprising administering to the subject a first composition comprising IL-2 and a second composition comprising an agent selected from the group consisting of histamine, histamine structural analogs having $H_2$-receptor activities, endogenous histamine releasing preparations, and non-histamine derivative $H_2$-receptor agonists, said agent and said IL-2 being administered in amounts and for a period of time effective to attain the desired effect.

This invention also relates to a method increasing the anti-tumor cell effect of IL-2 in a subject comprising co-administering to the subject with the IL-2 a composition comprising an agent selected from the group consisting of histamine, histamine structural analogs having $H_2$-receptor activities, endogenous histamine releasing preparations and non-histamine derivative $H_2$-receptor agonists, said agent and said IL-2 being administered in amounts and for a period of time effective to attain the desired effect.

Still part of this invention is an improvement to a method of inhibiting tumor growth and metastases malignant tumor cells in a subject carrying the cells with a composition comprising IL-2, the improvement comprising co-administering to the subject a composition comprising an agent selected from the group consisting of histamine, histamine structural analogs having $H_2$-receptor activities, endogenous histamine releasing preparations and non-histamine derivative $H_2$-receptor agonists; the IL-2 and the agent being administered in amounts and for a period of time effective to inhibit tumor growth and the metastases of the cells.

Also encompassed by this invention is an improvement to a method of treating a subject carrying malignant tumor cells with a composition comprising IL-2, the improvement comprising co-administering to the subject a composition comprising an agent selected from the group consisting of histamine, hisamine structural analogs having $H_2$-receptor activities, endogenous histamine releasing preparations, and non-histamine derivative $H_2$-receptor agonists, the agent and the IL-2 being administered in amounts and for a period of time effective to increase the anti-tumor effect of IL-2.

A more complete appreciation of the invention and many of the attendant advantages thereof will be readily perceived as the same becomes better understood by reference to the following detailed description when considered in connection with the accompanying figure.

Other objects, advantages and features of the present invention will become apparent to those skilled in the art from the following discussion.

BEST MODE FOR CARRYING OUT THE INVENTION

Figure 1:
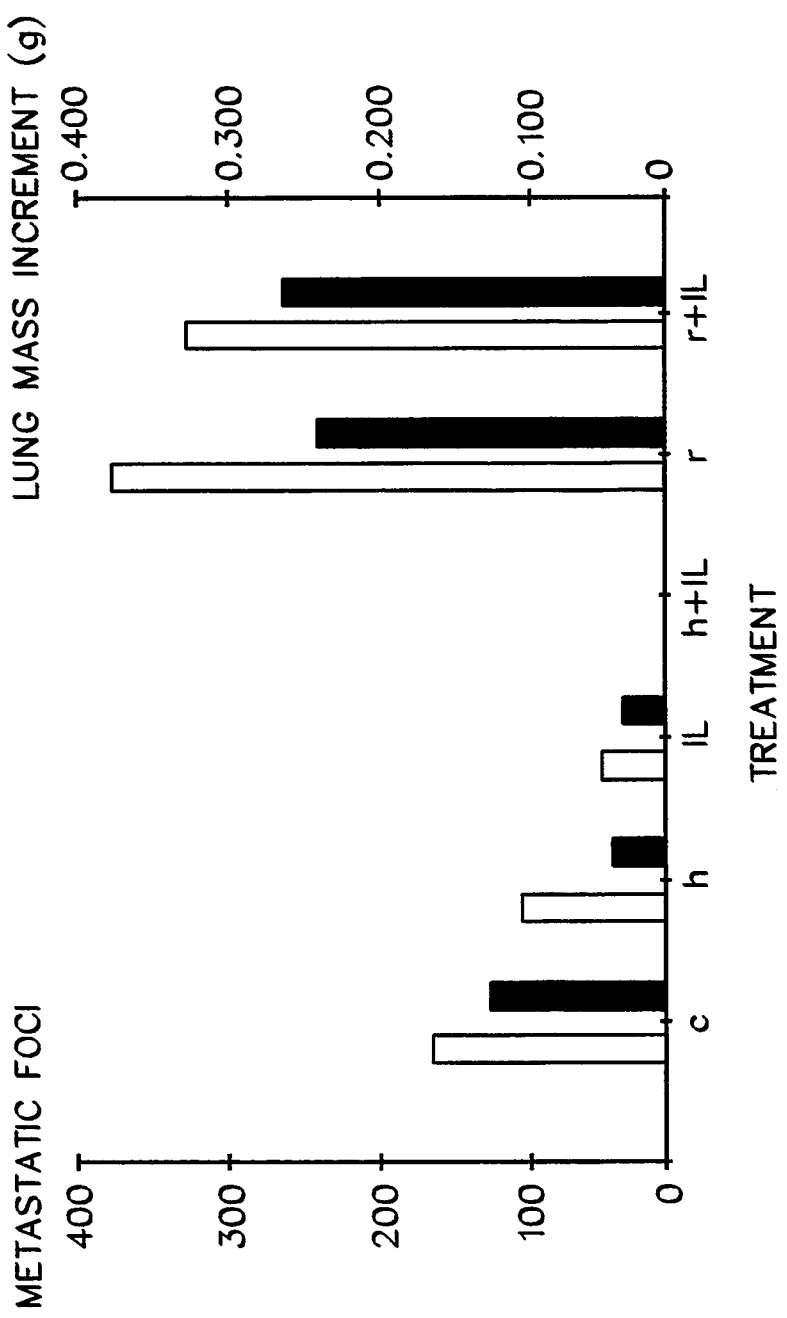
FIG. 1 is a histogram showing the number of lung metastatic foci of B16 melanoma cells produced by various treatments of male mice.

This invention arose from the unexpected in vitro findings that (i) IL-2 can suppress NKCC in the presence of monocytes, and (ii) histamine and IL-2 act synergistically with respect to NKCC enhancement.

These findings prompted the inventors to analyze the in vivo effects of combined histamine/IL-2 treatment on the formation of lung metastases in a mouse animal model.

This invention relates to a method of inhibiting tumor growth and the formation of metastases of malignant tumor cells in a subject carrying the cells comprising administering to the subject a first composition comprising IL-2 and a second composition comprising an agent selected from the group consisting of histamine, histamine structural analogs having $H_2$-receptor activities, endogenous histamine releasing preparations, and non-histamine derivative $H_2$-receptor agonists, said agent and said IL-2 being administered in amounts and for a period of time effective to attain the desired effect.

A histamine $H_2$-receptor agonist is a compound that binds to a histamine $H_2$-receptor on the surface of a cell and triggers the transduction of a signal over the cell membrane. The term $H_2$-receptor agonist includes agonist compounds structurally similar to histamine (histamine analogs) and agonists structurally unrelated to histamine. Histamine has $H_2$-receptor activity and so does histamine structurally similar derivatives such as 4-methyl histamine. Other $H_2$-receptor agonists are included, which are structurally unrelated to histamine, such as dimaprit. This pharmacological terminology is explained in more detail in "Chemistry and Structure-Activity Relationships of Drugs Acting as Histamine Receptors", *Pharmacology of Histamine Receptors*, Ganellin et al, John Wright & Sons, Bristol, pages 10–102 (1982).

This invention also relates to a method of increasing the anti-tumor cell effect of IL-2 in a subject comprising co-administering to the subject with the IL-2 a composition comprising an agent selected from the group consisting of histamine, histamine 1 structural analogs having $H_2$-receptor activities, endogenous histamine releasing preparations, and nonhistamine derivative $H_2$-receptor agonists, said agent and said IL-2 being administered in amounts and for a period of time effective to attain the desired effect.

Compounds referred to above as "endogenous histamine-releasing preparation" refer to compounds which cause the level of histamine in a subject to increase either by increasing histamine's production/release or by inhibiting histamine breakdown/elimination to increase levels of histamine in a subject as more is released. This is an alternative to directly treating with histamine. For example, these releasing compounds liberate intracellular stores of histamine either into the circulation of a subject or into the tissue of cells adjacent to histamine-containing cells. The administration of compounds which increase the level cf histamine in a subject induce effects similar to those noted after the administration of histamine. Examples of histamine releasing drugs are listed in "Factors Regulating Availability of Histamine at Tissue Receptors", *Pharmacology of Histamine Receptors*, Ganellin et al, John Wright & Sonc, Bristol, pages 103–145 (1982).

Still part of this invention is an improvement to a method of inhibiting tumor growth and metastases of malignant tumor cells in a subject carrying the cells with a composition comprising IL-2, the improvement comprising co-administering to the subject a composition comprising an agent selected from the group consisting of histamine, histamine structural analogs having $H_2$-receptor activities, endogenous histamine releasing preparations, and non-histamine derivative $H_2$-receptor agonists; the IL-2 and the agent being administered in amounts and for a period of time effective to inhibit tumor growth and the metastases of the cells.

Also encompassed by this invention is an improvement to a method of treating a subject carrying malignant tumor cells with a composition comprising IL-2, the improvement comprising co-administering to the subject a composition comprising an agent selected from the group consisting of histamine, histamine structural analogues having $H_2$-receptor activities, endogenous histamine releasing preparations, and non-histamine derivative $H_2$-receptor agonists, the agent and the IL-2 being administered in amounts and for a period of time effective to increase the anti-tumor effect of IL-2.

Figure 2:
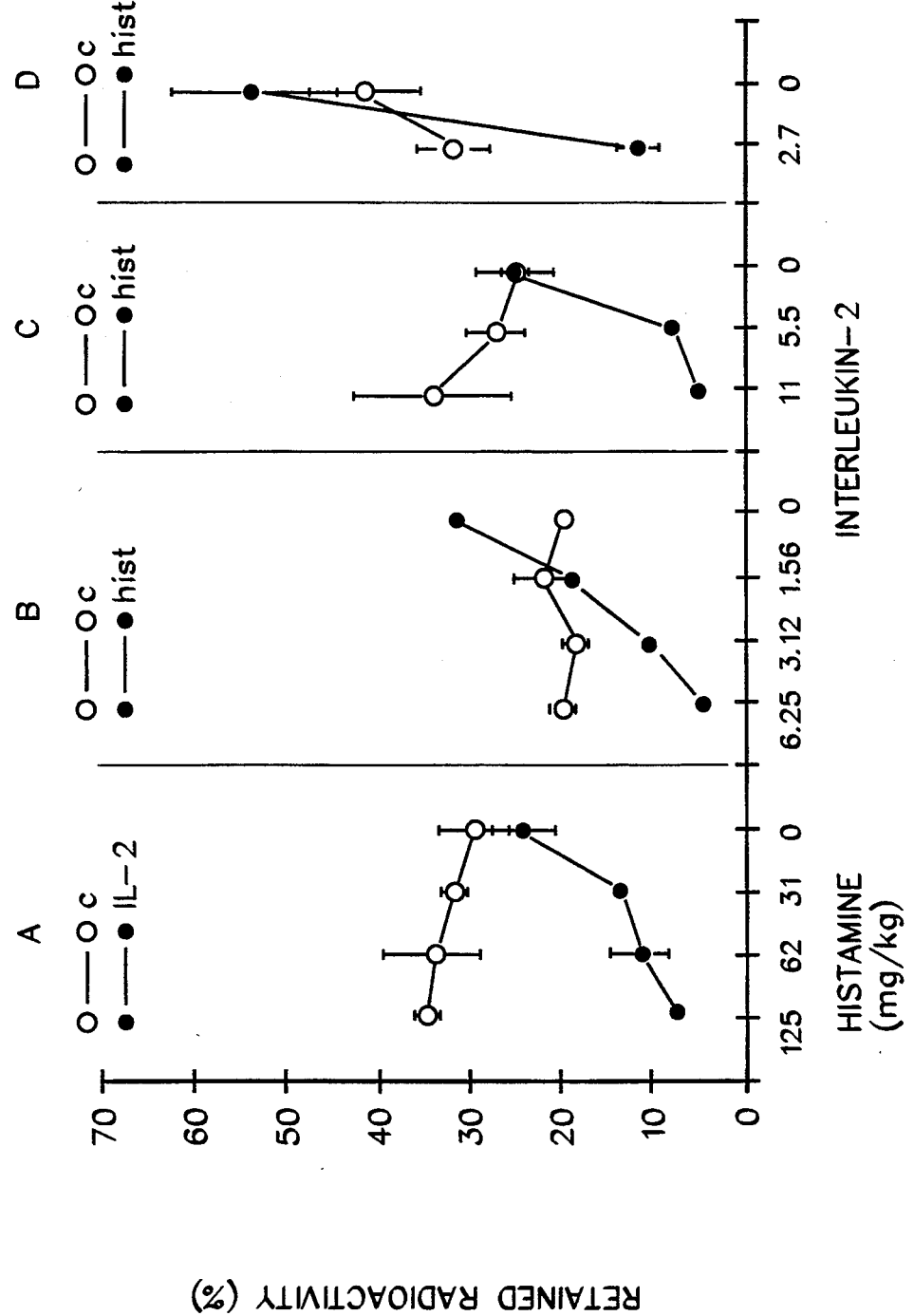
FIG. 2 shows that histamine and IL-2 synergistically augment the in vivo killing of K562 cells as well as YAC-1 lymphoma cells. Section 2A shows the results of treatment with 125, 62, 31 or 0 mg/kg histamine and either 6,250 U/kg IL-2 or control. Section 2B shows the results of treatment either $65.25 \times 10^3$, $3.12 \times 10^3$, $1.56 \times 10^3$, or 0 U/kg IL-2 and either 125 mg/kg histamine or control. Section 2C shows the results of treatment with $11 \times 10^3$, $5.5 \times 10^3$, or 0 U/kg IL-2 and either 125 mg/kg histamine or control. Section 2D shows the results of treatment with $2.7 \times 10^3$, or 0 U/kg IL-2 and either 250 mg/kg histamine or control.

A more complete appreciation of the invention and many of the attendant advantages thereof will be readily perceived as the same becomes better understood by reference to the following detailed description when considered in connection with the accompanying FIGS. 1 and 2 and Tables I and III.

Other objects, advantages and features of the present invention will become apparent to those skilled in the art from the following discussion.

Unexpectedly, a combined histamine/IL-2 treatment completely prevented metastasis of malignant tumor cells when the compounds were given as a single dose 24 hrs. prior to and one week after tumor cell inoculation. These are unexpectedly superior results since under similar circumstances neither IL-2 alone nor histamine alone had such beneficial effect. The doses of IL-2 used in the animal experiments were substantially lower than amounts used in general for treatment of cancer. This is of particular importance since the potentiation of the anti-tumor effect of IL-2 induced by concomitant treatment with histamine permits a reduction of the high doses of IL-2 which are used in cancer therapy. Such high-dose IL-2 treatment is associated with serious side-effects (Rosenberg, S. A., supra).

FIG. 1 is a histogram showing the number of lung metastatic foci of B16 melanoma cells produced by various treatments of male mice. The results are explained in Example 4, following the discussion below.

Provided herein is a method of inhibiting tumor growth and the metastases of malignant tumor cells in a subject carrying the cells comprising administering to the subject a first composition comprising an agent selected from the group consisting of histamine, histamine structural analogues having $H_2$-receptor activities, endogenous histamine releasing preparations and non-histamine derivative $H_2$-receptor agonists and a second composition comprising IL-2; said agent and said IL-2 being administered in amounts and for a period of time effective to attain the desired effect.

Analogs of histamine having $H_2$-receptor activities which are suitable for use in this invention are known in the art and need not be described herein. By means of example, the analogs may have a chemical structure similar to that of histamine but be modified by the addition of moieties which do not negatively interfere with their histamine-like activities, and in particular with their $H_2$-receptor activities. Examples of non-histamine derivative $H_2$-receptor agonists suitable for use in this invention are those such as dimaprit but not N-methyl-dimaprit or nor-dimaprit. Endogenous histamine releasing preparations suitable for use herein are known in the art. Examples of preparations capable of releasing endogenous histamine are these comprising other lymphokines such as IL-3 or allegens. However, other known preparations are also suitable.

IL-2 and compounds such as histamine, histamine structural analogs, endogenous histamine releasing preparations, and non-histamine derivative $H_2$-receptor agonists can be administered separately or in the same composition. The administration can be attained by routes which are known in the art for these compounds and preparations. By means of example they can be administered by local or systemic injection, or infusion, as is known in the art. However, other means of administration are also suitable.

The present compounds may also be administered by the intraperitoneal and other parenteral routes. Solutions of the active compound as a free acid or a pharmaceutically-acceptable salt may be administered in water with or without a surfactant such as hydroxypropyl cellulose. Dispersions are also contemplated such as those utilizing glycerol, liquid polyethylene glycols and mixtures thereof and oils. Antimicrobial compounds may also be added to the preparations. Injectable preparations may include sterile aqueous solutions or dispersions and powders which may be diluted or suspended in a sterile environment prior to use. Carriers such as solvents dispersion media containing, e.g., water, ethanol polyols, vegetable oils and the like, may also be added. Coatings such as lecithin and surfactants may be utilized to maintain the proper fluidity of the composition. Isotonic agents such as sugars or sodium chloride may also be added as well as products intended for the delay of absorption of the active compounds such as aluminum monostearate and gelatin. Sterile injectable solutions are prepared as is known in the art and filtered prior to storage and/or administration. Sterile powders may be vacuum dried freeze dried from a solution or suspension containing them.

Any material added to the pharmaceutical composition should be pharmaceutically-acceptable and substantially non-toxic in the amounts employed. Sustained-release preparations and formulations are also within the confines of this invention.

Pharmaceutically-acceptable carriers as utilized in the context of this patent include any and all solvents, dispersion media, coatings, antimicrobial agents, isotonic and absorption delaying agents and the like as is known in the art. All preparations are prepared in dosage unit forms for uniform dosage ana ease of administration. Each dosage unit form contains a predetermined quantity of active ingredient calculated to produce a desired therapeutic effect in association with a required amount of pharmaceutical carrier.

Typically, the agent which encompasses histamine, histamine structural analogs, endogenous histamine releasing preparations, and non-histamine derivative $H_2$-receptor agonists may be administered in an amount of about 0.1 to 10 mg/day, preferably about 0.5 to 8 mg/day, and more preferably about 1 to 5 mg/day. However, other amounts may also be administered with IL-2 as can be tailored by a practitioner.

Although in the examples the compounds are administered as a sole dose, it is understood that for anti-tumor therapies the compounds may be administered for prolonged periods of time. Typically, the treatment may be administered for periods of up to about 1 week, and even for periods greater than 1 month. In some instances after a period of anti-tumor treatment, the treatment may be discontinued and then resumed once again.

The IL-2 may be administered in an amount of about 1,000 to 300,000 U/kg/day, more preferably about 3,000 to 100,000 U/kg/day, and more preferably about 5,000 to 20,000 U/kg/day, or otherwise as known in the art.

A daily dose may be administered as one dose or it may be otherwise divided into several doses if negative effects are observed.

In one preferred embodiment of the method, the histamine, histamine structural analogs having $H_2$-receptor activities, endogenous histamine releasing preparations, or non-histamine derivative $H_2$-receptor agonist and the IL-2 are administered on the same days. A still more preferred embodiment of the method of the invention is one wherein the agent is histamine and the histamine is administered in the same composition with IL-2.

In another aspect of the invention it is provided herein a method of increasing the anti-tumor cell effect of IL-2 in a subject comprising co-administering to the subject a first composition comprising IL-2 and a second composition comprising an agent selected from the group consisting of histamine, histamine structural analogues having the $H_2$-receptor activities, endogenous histamine releasing preparations, and histamine derivative $H_2$-receptor agonists; the agent and the IL-2 being administered in amounts and for period of time effective to attain the desired effect.

As in the case of the prior method, the agent and the IL-2 may be administered separately or as a single composition. Typically, the agent is administered in an amount of about 0. 1 to 10 mg/day, more preferably about 0. 5 to 8 mg/day, and more preferably about 1 to 5 mg/day for a period of time of about 1 week to month, and in some instances for a period greater than 2 months. The IL-2 may be administered in an amount of about 1,000 to about 300,000 U/kg/day, more preferably about 3,000 to 100,000 U/kg/day, and more preferably about 5,000 to 20,000 U/kg/day, for a period of about week to 1 month, and in some cases the treatment may be prolonged for a period greater than about 2 months. The treatment with the two compounds may be discontinued for a period of time and then resumed as was described above. Other regimes and amounts may also be utilized.

Also provided herein is an improvement on a known method of treating a subject carrying a malignant tumor with a composition comprising IL-2, the improvement comprising co-administering to the subject a composition comprising an agent selected from the group consisting of histamine, histamine structural analogues having $H_2$-receptor activities, endogenous histamine releasing preparations and non-histamine derivative $H_2$-receptor agonists; the IL-2 and the agent being administered in amounts and for a period of time effective to potentiate the anti-metastatic effect of IL-2.

The agent may be administered in amounts as described above, or as an artisan with skill in the art can determine. Similarly, the IL-2 may be administered in amounts known in the art (higher than prescribed herein), as described herein or as an artisan may determine to be suitable for specific applications. Typically, the agent may be administered for a period of time of about 1 week and in some cases for even longer periods of time. Similarly the IL-2 may be administered for a period of time as is known in the art for specific types of tumors or about 1 week to 2 months, and in many instances for longer periods of time as well.

In a particularly preferred embodiment of the method, the agent and the IL-2 are administered on the same days for increased potentiation of their mutual effects.

Also provided herein is an improvement on a method of inhibiting tumor growth and the metastases of malignant tumor cells in a subject carrying the cells with a composition comprising IL-2, the improvement comprising co-administering to the subject a composition comprising an agent selected from the group consisting of histamine, histamine structural analogues having $H_2$-receptor activities, endogenous histamine releasing preparations, and non-histamine derivative $H_2$-receptor agonists, the agent being administered in amounts and for a period of time effective to increase the anti-tumor effect of IL-2 and to prevent the metastases of the cells.

Typically, the agent is administered in an amount of 0.1 to 10 mg/day, more preferably about 0.5 to 8 mg/day and more preferably about 1 to 5 mg/day. The IL-2 is administered as known in the art or in an amount of about 1,000 to 300,000 U/kg/day, more preferably about 3,000 to 100,000 U/kg/day and more preferably about 5,000 to 20,000 U/kg/day. The two compounds may be administered separately or in the same composition as described above.

In one preferred embodiment the agent and the IL-2 are administered on the same days and as a sole composition. This therapy may be continued for a period of up to about 1 week, and even for periods longer than about 4 weeks. Rest periods flanked by treatment periods may-also be utilized.

The present methods may be utilized alone or in conjunction with other anti-cancer therapies as seen suitable by a practitioner.

Having now generally described this invention, the same will be better understood by reference to certain specific examples, which are included herein for purposes of illustration only and are not intended to be limiting of the invention or any embodiment thereof, unless so specified.

EXAMPLES

Example 1: In vitro Studies with IL-2 and Histamine

This example provides a study on the effects of histamine, ranitidine and recombinant IL-2 (25U/ml), alone or in combination, on the NK-cell cytotoxicity (NKCC) of human mononuclear cells (MNC).

The MNC were obtained from peripheral venous blood of healthy blood donors and recovered Ficoll-Hypag centrifugation followed by Percoll density gradient fractionation as previously described (Hellstrand, K. et al. J. Immunol. 137:656 (1986)). A low density Percoll fraction 8 used in the experiments contained approximately 30% monocytes and was enriched for large granular lymphocytes (LGL).

N KCC was measured in a $^{51}$Cr-release microcytotoxicity assay using K562 erythroleukemia, Daudi B-lymphoblastoid, Molt-4 T cells, and Chang liver cells as target cells (all malignant cells).

NKCC was determined in sextuplicate as specific Cr-release at a MNC:target cell ratio of 15:1 or 30:1. The assays were performed in Iscove's medium containing antibiotics and 10% human AB+serum. Histamine, IL-2, and ranitidine or various combinations thereof (see Table below) were added at the onset of a 4 hr $^{51}$Cr-release assay. Control cells were given vehicle only.

The results obtained were as follows. Histamine ($10^{-4} - 10^{-7}$ M) augmented NK cell cytotoxicity against all types of tumor cells in the presence of monocytes. This effect was entirely blocked by equimolar concentrations of ranitidine. Ranitidine alone did not affect NKCC. In the absence of monocytes, i.e., after removal of monocytes by 1 hr incubation of the MNC on a Petri dish or by carbonyl iron treatment, histamine, ranitidine, or histamine plus ranitidine were devoid of effects at any concentration tested.

IL-2 (5–50 U/ml) alone was unexpectedly ineffective or even suppressed NKCC in the presence of monocytes. After removal of monocytes, IL-2 strongly augmented NKCC dose-dependently over the same range of concentrations. Histamine, ranitidine or histamine plus ranitidine did not affect IL-2-induced enhancement of NKCC in monocyte-depleted MNC. However, histamine plus IL-2 yielded a strong synergistic enhancement of NKCC in the presence of monocytes against all tumor cell targets tested. This synergistic effect was entirely blocked by the presence of ranitidine. Results of a representative experiment are shown in a Table below.

TABLE I

Demonstration of Synergistic Activation of Human NKCC by Combined Treatment with Histamine and IL-2

| Treatment[1] | NKCC (cell lysis %) ± s.e.m.) against respective tumor target cells | | | |
|---|---|---|---|---|
| | K562 | Daudi | Chang | Molt-4 |
| medium | 21.6 ± 1.2 | 3.9 ± 1.1 | 17.4 ± 1.1 | 11.8 ± 0.5 |
| Hist($10^{-5}$M) | 35.9 ± 0.9 | 12.8 ± 1.0 | 32.1 ± 2.0 | 43.2 ± 1.5 |

TABLE I-continued

Demonstration of Synergistic Activation of Human NKCC by Combined Treatment with Histamine and IL-2

| Treatment[1] | NKCC (cell lysis %) ± s.e.m.) against respective tumor target cells | | | |
|---|---|---|---|---|
| | K562 | Daudi | Chang | Molt-4 |
| IL-2 (25 U/ml) | 12.0 ± 0.7 | 1.4 ± 0.5 | 9.8 ± 0.6 | 5.2 ± 0.4 |
| Ran ($10^{-5}$M) | 20.8 ± 1.9 | 4.3 ± 0.8 | 19.7 ± 1.3 | 13.0 ± 1.0 |
| Hist + IL-2 | 55.4 ± 1.0 | 41.4 ± 0.9 | 59.7 ± 0.6 | 69.4 ± 3.0 |
| Hist + Ran | 20.1 ± 1.4 | 5.0 ± 1.4 | 19.4 ± 1.0 | 13.0 ± 1.1 |
| Ran + IL-2 | 11.3 ± 1.3 | 1.9 ± 0.3 | 10.4 ± 0.9 | 6.4 ± 0.7 |
| Hist + Ran + IL-2 | 13.4 ± 2.0 | 2.0 ± 0.7 | 10.0 ± 0.5 | 8.0 ± 1.1 |

[1]Effector MNC were recovered from peripheral blood by Ficoll-Hypaque and Percoll density gradient centrifugation. A low density Percoll fraction with 27% monocytes was used at a final effector to target cell ratio of 15:1 (K562 Chang, and Molt-4) or 30:1 (Daudi).
[2]Hist = histamine, IL-2 = interleukin-2 Ran = Ranitidine Example 2: In vivo Studies Model of Antitumor Effects of Histamine, IL-2, Ranitidine and Combinations of these Compounds in a Mouse Tumor Animal Model In vivo experiments were carried out with histamine or IL-2 alone, and with combinations of these compounds in a mouse tumor animal model.

Histamine (25 mg/kg), ranitidine (25 mg/kg), and human recombinant IL-2 (6,000 U/kg), alone or in combination, were administered, H i.v. as a single-dose to 4–6 weeks old male Swiss albino mice (20 g) 24 hours prior to and 1 week after intravenous inoculation B16 mouse melanoma cells (150,000 cells/mouse). Each treatment group comprised 10 animals. Twenty-four hours after treatment, NK-cell sensitive B16 mouse melanoma cells (150,000 cells/mouse) were inoculated intravenously. Controls were run with animals treated with the respective drug vehicles.

Lung metastatic foci (LMF) on the surface of the lungs were monitored macroscopically 21 days later. LMF were counted by an unbiased observer using a 10×magnifying microscope. All LMF visible on the lung surface were counted.

The weights of the lungs were measured immediately after sacrifice of the mice and correlated in a virtually linear fashion to the number of LMF.

Example 3: Results of the Tests Conducted in Example 2

Using the therapeutic regimen depicted in Example 2, histamine alone was found to relatively effectively reduce the number of LMF. 25 mg/kg of histamine yielded approximately an about 50% reduction whereas 250 mg/kg of histamine yielded an about 80–90% reduction of LMF.

This effect was mimicked by dimaprit with similar potency.

Ranitidine augmented LMF by about 100%.

IL-2 alone reduced LMF by about 40–70%.

The combined treatment with histamine (25 mg/kg) and IL-2 completely prevented LMF (see the Figure). None of the animals (n=10) treated with histamine (25 mg/kg)+IL-2 ($6 \times 10^3$ U/kg) displayed visible tumors. None of the animals (n=10) treated with histamine (25 mg/kg) or IL-2 ($6 \times 10^3$ U/kg) alone were completely free of visible tumors. IL-2 was virtually ineffective in the presence of ranitidine. The lung weights of animals receiving histamine plus IL-2 was equal to the weight of lungs from mice that had not been subject to tumor cell inoculation. Histamine, IL-2 or histamine plus IL-2 was found not to affect lung weight of animals which did not receive tumor cells.

Example 4

The treatments represented in FIG. 1 showing the number of lung metastatic foci of B16 melanoma cells produced various treatment of male mice were conducted with a vehicle (c, control), 25 mg/kg histamine (h), $6 \times 10^3$ U/kg human recombinant IL-2 (IL), 25 mg/kg histamine+$6 \times 10$ U/kg human recombinant IL-2 (h+IL), 25 mg/kg ranitidine (r), $6 \times 10^3$ U/kg human recombinant IL-2 +25 mg/kg ranitidine (r+IL). The compositions were injected i.v. to 4–6 week old male Swiss albino mice and $1.5 \times 10$ B16 melanoma cells were injected i.v. to the mice 24 hours later. Treatment with vehicle. histamine, IL-2 , ranitidine, histamine+IL-2, and ranitidine+IL-2 was repeated 1 week after tumor inoculation. The lung metastatic foci (LMF) were monitored after sacrifice of the animals 21 days later. Open bars represents the mean number of LMF on the lung surface calculated from 10 animals per treatment.

Similar results were obtained in two separate experiments. The filled bars show lung weights of the respective treatment groups. The weights of lungs correlated to the number of LMF. As seen in FIG. 1, the lung weight of animals treated with histamine+IL-2 was equal to that of normal, tumor-free lungs.

Example 5

The following tests were conducted which show that human cancer cells are killed in vivo by treatment with histamine and IL-2. The test protocol is an established assay for killing of tumor cells in vivo and uses human leukemic cancer cells (K562 cells). The K562 cells were labeled with radioactivity and injected into a lateral tail vein of mice. The tumor cells are retained in the vasculature of the lung. If killing of a cell occurs, the remaining radioactivity in lung tissue is concomitantly reduced. FIG. 2, which is attached, illustrates the data from procedures A, B, C, and D and shows that histamine and IL-2 synergistically augment the in vivo killing of human K562 cells as well as mouse YAC-1 lymphoma cells.

The methods were as follows:

A. Animals: Swiss albino mice were obtained from breeding colonies at the Dept. of Virology, University of Göteborg. All food, bedding, and cage materials were presterilized. Experiments were conducted with 4–10 week old mice.

B. Tumor cells: YAC-1 murine lymphoma cells (Hanna & Fidler, JNCI, 65:801–810, 1980) were used. The cells were maintained in vitro by subculturing the tumor cells at 37° C. at a concentration of 105/ml in 50 ml tissue culture flasks (Costar, Cambridge, USA) in culture medium i.e., Iscove's medium supplemented with 10% heat-inactivated foetal calf serum (FCS), 1% L-glutamine, 1% sodium pyruvate, 50 µg/ml streptomycin, and 100 U/ml penicillin. Alternatively, human leukemic K562 cells (Lozzio & Lozzio, Blood 45:321–333, 1975) were used. These cells were maintained in vitro under similar culture conditions.

C. Compounds: Histamine dihydrochloride (Sigma Chemical Company, St. Louis, USA) and/or human recombinant IL-2 (EuroCetus, Amsterdam, Holland) were used. All reported IL-2 units are BRPM U; one BRPM U of IL-2 is equal to 2.25 IU. The compounds were readily dissolved in Iscove's medium. Animals injected with corresponding volumes of Iscove's medium were used as controls. Histamine and/or IL-2 were administered i.v. in 0.5 ml as single doses 6 h before i.v. tumor cell inoculation.

D. In vivo analysis of cytotoxicity against tumor cells in vivo: The method used was similar to that described by Hellstrand, Asea, and Hermodsson (Journal of Immunology 145:4365–4370, 1990). Briefly, $10^5$ $^{51}$Cr-labelled murine YAC-1 or human K562 cells were injected i.v. 6 h after one dose of treatment with histamine and/or IL-2 in vivo. Two hours after tumor cell inoculation, the mice were sacrificed by cervical dislocation. The in vivo cytotoxicity against the injected tumor cells was calculated by determination of retained radioactivity (%) in lungs.

The results of the four separate experiments are shown in FIG. 2, below, as A-D. All data shown are retained radioactivity (%) in the lungs 2 hours after tumor cell inoculation, as described above. The data points mean the ±s.e.m. of at the least 5 animals. Experiments A, B, and C were done with YAC-1 murine lymphoma cells, and experiment D was done with human K562 leukemic cells.

A. In experiment A animals were treated with histamine (125, 62, 31, or 0 mg/kg, as indicated on the abscissa) concomitantly with 6,250 U/kg IL-2(IL-2; filled circles) or culture medium [c(control);open circles].

B. In experiment B, animals were treated with IL-2($6.25 \times 10^3$, $3.12 \times 10^3$, $1.56 \times 10^3$, or 0 U/kg, as indicated on the abscissa) concomitantly with 125 mg/kg histamine (hist; filled circles) or culture medium (c; open circles).

C. In experiment C, animals were treated with IL-2 ($11 \times 10^3$, $5.5 \times 10^3$ or 0 U/kg as indicated on the abscissa) concomitantly with 125 mg/kg histamine (hist; filled circles) or culture medium (c; open circles).

D. In experiment D, animals were treated with IL-2 ($2.7 \times 10^3$ or 0 U/kg, as indicated on the abscissa) concomitantly with 250 mg/kg histamine (hist; filled circles) or culture medium (c; open circles).

See attached FIG. 2, Sections A, B, C, and D, which is based on the above experiments.

The data presented by FIG. 2 shows that combined treatment of mice with histamine and IL-2 synergistically augment rejection of human and murine tumor cells from lungs in vivo.

EXAMPLE 6

Treatment of purified human NK-cells with IL-2 augment the capacity of NK-cells to kill many types of human tumor cells in vivo (Domzig, W., et al, *The Journal of Immununology*, vol 130, pp. 1970–1973; reviewed by Trinichieri, G. *Advances in Immunology*, vol. 47, pp. 1870–376). To address the question of whether this activation of human tumor cell killing can occur also in vitro, it must be taken into consideration that the tumor is surrounded by several types of leukocytes apart from NK cells. These leukocytes may alter the activation of NK-cells induced by IL-2, and factors that regulate such communication between leukocyte subsets and NK-cells may determine the anti-tumor response of NK-cells to IL-2.

Granulocytes are a subset of leukocytes that are frequently detected in tumors and in tissues surrounding tumors. To study the role of granulocytes for the effects of histamine and IL-2 on killing of human tumor cells in vitro, autologous granulocytes were added to enriched human NK-cells. The granulocytes were enriched to 95% purity using the counter-current centrifugal elutriation technique described in Hellstrand, K, et al, Scand. J. Immunol. vol. 34, pp. 741-752, NK-cells were recovered from peripheral blood using Percoll density gradient centrifugation as described in Hellstrand K, et al, Sacnd J. Immunol. roll 34, pp. 741-752.

As shogun in Table II below, the addition of granulocytes to NK-cells markedly suppressed the antitumor cytotoxicity against K 562 leukemic target cells exerted by NK-cells and completely abrogated the activation of NK-cells induced by IL-2. Combined treatment with histamine and IL-2 synergistically augmented the killing of tumor cells (Table II).

In conclusion, these experimental data, presented in Table II, show that histamine and IL-2 synergistically augment the anti-tumor cytotoxicity of NK-cells in a mixture of granulocytes and NK-cells. The presence of granulocytes in tumors and surrounding tissues in vivo most probably will blunt an NK-cell response to IL-2. However, in the presence of histamine, activation of NK-cell anti-tumor cytotoxicity by IL-2 is allowed to occur.

The data described above is presented by Table II, below. Human NK-cell cytotoxicity was recorded as cell lysis %, as described in Hellstranc, K, et al. The Journal of Immunology, vol. 143, pp. 4095-4099, K 562 leukemic cells were used as target cells (Trinchieri, G., Advances in Immunology, vol. 47, pp. 187-376). The term NK-cells refers to NK-cells enriched by Percoll density gradient centrifugation. More than 90% of the recorded cytotoxicity was mediated by NK-cells as described in Hellstrand, K., et al, Journal of Interferon Research (in press). Presented are the ±standard error of the mean of sextuplicate determinations.

TABLE II

| cells | NK-cell anti-tumor cytotoxicity after treatment with | | | |
|---|---|---|---|---|
| | medium | histamine | IL-2 | histamine IL-2 |
| NK-cells | 44.2 ± 1.1 | 43.8 ± 1.8 | 50.5 ± 1.5 | 51.3 ± 1.9 |
| granulocytes | <1 | <1 | <1 | <1 |
| NK-cells + granuloctyes | 10.6 ± 1.2 | 19.8 ± 2.4 | 8.0 ± 1.3 | 34.9 ± 1.7 |

Example 7

Animals

C57BL/6, BALP/c, and Swiss albino mice were obtained from breeding colonies at the Department of Virology, University of Göteborg. Adult 98-wk-old) C57BL/6 nude mice (nu/nu-C57BL/6JBom) were purchased from Bornmice A/S, Ry, Denmark. All food, bedding, and cage materials were presterilized. Experiments were conducted with 6- to 12-week-old female mice.

Tumor cells

B16, a murine melanoma that is syngeneic to C57BL/6 mice, was used, B16 strains with a high (F10) and intermediate (F1) metastatic potential were provided by Dr. Walter Ryd. Department of Pathology, University of G6teborg, and Dr. Terje Kalland, Department of Anatomy, University of Lund, Sweden. The B16-F1 cells were maintained in vivo by serial i.p. passages of $10^6$ tumor cells and in vitro by subculturing the tumor cells at 37° C. at a concentration of $10^6$/ml in 50-ml tissue culture flasks (Costar, Cambridge, MA) in culture medium, i.e., Iscove's medium supplemented with 10% heat-inactivated FCS, 1% L-glutamine, 1% sodium pyruvate, 50 μg/ml streptomycin, and 10 U/ml penicillin. B16-F10 and YAC-1 lymphoma cells were maintained in vitro under similar culture conditions.

Compounds

Histamine dihydrochloride (Sigma Chemicals, Stockholm, Sweden), dimaprit dihydrochloride (and $H_2R$-agonist; kindly provided by Smith Kline & French, Hertforshire, England), nor dimaprit (and $H_2R$-inactive chemical control to dimaprit; SK&F), 2-thiazolylethylamide an $H_1R$ agonist; provided by Dr Lars Edvinson, Lund), and the $H_2R$ antagonists rantidine hydrochloride (Glaxo; obtained from the commercially available vial), cimetidine hydrochloride (SK&F: obtained from the commercially available vial), famotidine (obtained from the commercially available vial: Merck Sharp & Dohme), and tiotidine hydrochloride (ICI-Pharma AB, Goteborg, Sweden) were used (for a review of the pharmacology of histaminergic agonists/antagonists, see Ref. 5), Human rIL-2[sp. act..$3 \times 10''$ BRPM U/mg protein) was purchased from Genzyme, Stockholm, Sweden. All reported IL-2 units are BRPM U of IL-2 is equal to 2.25 IU. All compounds were readily dissolved in Iscove's medium. Animals injected with corresponding volumes of Iscove's medium were used as controls. If not otherwise stated, histamine receptor agonists/antagonists or IL-2 were administered i. v. in 0.5 ml single doses 24 h before i.v. TCI.

Monitoring of tumor parameters

Fourteen to 21 days of TCI, all macroscopically visible PMF were counted under a light microscope. TM was calculated as the wet weight (mg) of tumor-bearing lungs after substraction of the lung weight of corresponding tumor-free animals.

In vivo Depletion of NK cells

NK cells were depleted by treatment with antibodies to asialo-GMI (lot No. PDG 9536; purchased from Wake Chemicals, News. FRGI), a glycolipid antigen expressed on mouse NK cells (6). Twenty μl of asialo-GM1 in 0.5 ml was injected into a lateral tail vein of respective mice. This method depleted all detectable cytotoxicity against YAC-1 cells of spleen and Ficoli Hypaque-separated PBMC in vitro (data not shown) and effectively reduced in vivo clearance of YAC-1 cells (see FIG. 3 below) in accordance with several earlier reports (reviewed in Ref. 4).

In vivo analysis of NK cell cytotoxicity

The method used was similar to that described by Hanna and Figler. Briefly, $10^8$ $^{81}$Cr-labeled YAC-1 cells were injected i.v. 24 h after treatment with $H_2R$ interactive compounds in vivo. At 4 h after TCL the mice were sacrificed by cervical dislocation. NK cytotoxicity was calculated by determination of retained radioactivity in lung tissue after injection of labeled tumor cells in NK-sufficient and NK cell-depleted (anti-asialo-GMl-treated animals. In vivo NK cell activity is expressed as the percentage of radioactivity retained in lungs at time zero ($1.64 \times 10°$ cpm (mean of nine separate experiments, range $0.92-2.01 \times 10^8$ _ after TCI Statistical evaluation For statistical evaluation of tumor parameters (PMF/TM) and NK cytotoxicity, analysis of variance followed by Fisher's exact probability test. The Wilcoxon rank sum test or the Mann-Whitney U-test were used. The $X^2$ was used for frequency comparisons. All indicated p values are two sided.

Effects of histamine and ranitidine on antimetastatic effects of I1-2

A single i.v. of a low dose of rIL-2 (6000 U/kg), administered 24 h before TCI reduced B16 PMF formation (Table III). A relatively low dose of histamine (25 mg/kg) consistently potentiated antitumor effects of rIL-2 using both F1 and F10 B16 cells with F1 cells, combined histamine/IL-2 treatment completely prevented metastasis in repeated experiments o Concomitant treatment with ranitidine abrogated the antitumor effect of rIL-2; animals receiving ranitidine and IL-2 displayed the same level of enhanced metastasis as those treated with ranitidine (Table III).

nant effect of pharmacologic treatment with histamine on NK cell cytotoxicity in vivo is activatory rather than suppressive.

IL-2, a T cell-derived lymphokine, effectively activates NK cells and exerts antitumor effects in mice by a mechanism that requires intact NK cells. The finding that IL-2 treatment reduced B16 metastasis is consistent with earlier reports of antitumor efficacy of this compound in the B16 melanoma model. The above results show that concomitant treatment with histamine and IL-2 synergistically eliminated B16 metastases in repeated experiments. By contrast, ranitidine treatment apparently blocked antitumor effects of IL-2. These findings are in line with the demonstration that histamine and IL-2 synergistically activate human NK cells in vitro. Further, ranitidine or other $H_2R$ antagonists used as adjuvants in several human anticancer trials using IL-2, mainly to ameliorate gastrointestinal side effects of IL-2 and to block a putative histamine $H_2R$ mediated immunosuppression. The efficacy of $H_2$-receptor antagonists in IL-2 therapy has not been evaluated; the results of the present study suggest that $H_2R$

TABLE III

HISTAMINE ACTIVATES NK CELLS IN VIVO
EFFECTS OF HISTAMINE, RANITIDINE, AND I1-2 ON b16 MELANOMA METASTASIS IN VIVO

| Expt no. a | Mouse/B16 Strain | Tumor Parameter | Lung Tumors after Treatment[a] with | | | | | |
|---|---|---|---|---|---|---|---|---|
| | | | Control | Histamine | Ranitidine | IL-2 | Histamine + IL-2 | Ranitidine + IL-2 |
| 1[b] | Swiss/F1 | PMF[c] | 159 ± 43 | 41 ± 16 | 363 ± 63 | 44 ± 11 | 0 | 320 ± 56 |
| | | TM[c] | 116 ± 36 | 37 ± 21 | 231 ± 63 | 29 ± 24 | 0 ± 0.3 | 257 ± 14 |
| 2[b] | Swiss/F1 | PMF | 32 ± 7 | 14 ± 2 | 319 ± 79 | 8 ± 3 | 0 | 375 ± 78 |
| | | TM | 15 ± 4 | 7 ± 1 | 295 ± 85 | 7 ± 4 | 0 ± 0.4 | 3267 ± 85 |
| 3[b] | Swiss/F1 | PMF | 49 ± 9 | 19 ± 3 | ND | 16 ± 2 | 0 | ND |
| | | TM | 93 ± 10 | 74 ± 19 | ND | 38 ± 12 | 0 ± 10 | ND |
| 4[b] | Swiss/F10 | PMF | 547 ± 71 | 232 ± 61 | >700 | 255 ± 49 | 38 ± 10 | ND |
| | | TM | 261 ± 31 | 89 ± 39 | 477 ± 69 | 92 ± 10 | 9 ± 3 | ND |
| 5[b] | C57B/F10 | PMF | 171 ± 20 | 73 ± 14 | >500 | 84 ± 17 | 3 ± 2 | ND |
| | | TM | 131 ± 15 | 53 ± 16 | 497 ± 79 | 79 ± 8 | 1 ± 0.5 | ND |

[a]All compounds were administered i.v. as a single dose 24 hours before i.v. inoculation of $10^5$ B16 melanoma cells (histamine, 25 mg/kg; ranitidine, 50 mg/kg; IL02, 6000 U/kg'. The results shown were obtained in five separate experiments.
[b]Statistical evaluation (PMF values, Mann-Whitney U-test): Expt. 1-3; control vs histamine, IL-2, ranitidine, histamine or IL-2; or ranitidine + IL-2; p < 0.01; histamine + IL-2 vs histamine or IL-2; p < j0.01; ranitidine + IL-2 vs histamine or IL-2; p c 0.01 Expt 5; control vs histamine IL-2 or histamine/IL-2; p > 0.01; control vs ranitidine; p 0.05 histamine/ IL-2 vs. histamine or IL-2; p <0.01
[d]ND not done The results in Table III show that in vivo treatment with histamine augments the antitumor reactivity of NK cells in vivo and reduces the formation of lung metastases by NK cell-sensitive melanoma cells by a mechanism that requires intact NK cells. Both of these effects of histamine were $H_2R$-specific, as indicated by mimicry exerted by specific $H_2R$ agonists and blocking by $H_2R$ antagonists. Treatment with $H_2R$ antagonists alone induced reciprocal effects as compared with histamine, i.e., reduction of the antitumor reactivity of NK cells and enhancement of B16 metastasis, thus indicating that endogenous stores of histamine may have a role in NK cell-mediated defense against neoplastic cells.

The concept that histamine activates NK cells is supported by earlier results obtained with human NK cells in vitro; histamine (acting via $H_2R$) has been shown to activate NK cell cytotoxicity by a mechanism of action involving a cell-to-cell mediated interaction between monocytes and phenotypically distinct NK cells. In contrast, activation of $H_2R$ also has been reported to suppress human NK cells in vitro. Thus, histamine induces the formation of an immunosuppressive protein (histamine-induced soluble suppressor factor), elaborated by T cells, which suppresses the cytotoxicity of enriched NK cells. The findings in the above experiment as shown in Table III suggest that the predominant agonists, rather than antagonists are useful in human antitumor therapy with IL-2.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation.

What is claimed is:

1. A method of augmenting natural killer cell cytotoxicity in a subject carrying malignant tumor cells, comprising administering to the subject:
   a first composition comprising an agent selected from the group consisting of histamine, a histamine structural analog having $H_2$-receptor activities, an endogenous histamine releasing preparation and a non-histamine derivative $H_2$-receptor agonist; and
   a second composition comprising interleukin-2;

said agent and said interleukin-2 being administered in amounts and for a period of time effective to augment natural killer cell cytotoxicity.

2. The method of claim 1, wherein the agent is administered in an amount of 1 to 10 mg/day.

3. The method of claim 1, wherein the agent is administered for a period of time of 1 to 4 weeks.

4. The method of claim 1, wherein the interleukin-2 is administered in an amount of 5,000 to 300,000 U/kg/day.

5. The method of claim 1, wherein the interleukin-2 is administered for a period of time of 1 day to 4 weeks.

6. The method of claim 1, wherein the agent and the interleukin-2 are administered on the same days.

7. The method of claim 1, wherein the agent is histamine.

8. In a method of treating a subject carrying malignant tumor cells with a composition comprising interleukin-2, the improvement comprising:

co-administering to the subject, with the interleukin-2, a composition comprising an agent selected from the group consisting of histamine, a histamine structural analog having $H_2$-receptor activities, an endogeneous histamine releasing preparation and a non-histamine derivative $H_2$-receptor agonist;

the interleukin-2 and the agent being administered in amounts and for a period of time effective to augment natural killer cell cytotoxicity.

9. The method of claim 8, wherein the agent is administered in an amount of 1 to 10 mg/day.

10. The method of claim 8, wherein the agent is administered for a period of time of 1 day to 4 weeks.

11. The method of claim 8, wherein the interleukin-2 is administered in an amount of 5,000 to 300,000 U/kg/day.

12. The method of claim 8, wherein the interleukin-2 is administered for a period of time of 1 day to 4 weeks.

13. The method of claim 8, wherein the agent and the interleukin-2 are administered on the same days.

14. The method of claim 8, wherein the agent is histamine.

15. A method for augmenting natural killer cell cytotoxicity comprising the steps of:

administering the following to a population of cells which includes lymphocytes and monocytes:
(a) an effective amount f interleukin-2; and
(b) a compound selected from the group consisting histamine, histamine structural analog having $H_2$-receptor activities, an endogenous histamine releasing preparation and a non-histamine derivative $H_2$-receptor agonist.

16. The method of claim 15, wherein said population of cells is located in vitro.

17. The method of claim 15, wherein said population of cells is located in vivo.

18. The method of claim 15, wherein the administration of said interleukin-2 and said compound is performed simultaneously.

19. The method of claim 15, wherein the administration of said interleukin-2 and said compound is performed on the same day.

20. The method of claim 17, wherein the interleukin-2 is administered in an amount of from 5,000 to 300,000 U/kg/day.

21. The method of claim 17, wherein the interleukin-2 is administered of a period of time from 1 day to about 4 weeks.

22. The method of claim 17, wherein the compound is administered in an amount of 1 to 10 mg/day.

23. The method of claim 17, wherein the compound is administered for a period of time from 1 day to 4 weeks.

* * * * *

UNITED STATES PATENT AND TRADEMARK OFFICE
CERTIFICATE OF CORRECTION

PATENT NO. : 5,348,739            Page 1 of 5
DATED : September 20, 1994
INVENTOR(S) : Jan U. K. Hellstrand, et al It is certified that error appears in the above-indentified patent and that said Letters Patent is hereby corrected as shown below:

On title page, item [73] Assignee: change "Suntello" to
--Syntello--.

Item [56] "References Cited" in the article by Richtsmeier,
please replace "Anol." with --Annal.--.

Item [57] Abstract, line 3, insert cells between
"carrying" and --the--.

Line 6, replace "analogs" with
--analog--.

Under "OTHER PUBLICATIONS" page 2, col. 1, line 3,
replace "Mediating" with --Mediated--.

under "Other Publications," column 1, line 24, please insert --NK Cell-- between "Synergistic" and "Activation" and delete "of Human NKCC".

under "Other Publications," column 1, line 37, please delete the equal sign and insert --+--.

under "Other Publications," column 1, line 41, insert a space between "Biogenic" and "Amines".

under "Other Publications," column 2, line 19, please replace "Metastic" with --Metastatic--.

under "Other Publications," column 2, line 34, please delete the word "published".

On page 3, under "Other Publications," column 1, line 3, please replace "Stemk" with --Stem--.

UNITED STATES PATENT AND TRADEMARK OFFICE
CERTIFICATE OF CORRECTION

PATENT NO. : 5,348,739

DATED : September 20, 1994

INVENTOR(S) : Jan U. K. Hellstrand, et al

It is certified that error appears in the above-indentified patent and that said Letters Patent is hereby corrected as shown below:

On page 3, under "Other Publications," column 2, line 14, please replace "Hallstrand" with --Hellstrand et al--.

On page 3, under "Other Publications," column 2, line 15, please insert a space between the alpha sign and "by".

In column 1, line 53, please replace "H$^1$" with --H$_1$--.

In column 3, line 63, please replace "hisamine" with --histamine--.

In column 5, line 20, please replace "cf" with --of--.

In column 5, line 21, please replace "induce" with --induces--.

In column 5, line 57, please replace "I and III" with --I through III--.

In column 6, line 37, please replace "allegens" with --allergens--.

In column 8, line 68, please delete the hyphen between "may" and "also".

In column 9, line 29, please insert "human" between "all" and "malignant".

In column 9, line 58, please replace "a table" with --Table I--.

In column 10, line 20, please delete the words "model of".

In column 10, line 54, please replace "an about" with --up to--.

In column 10, line 60, please insert the words --the formation of-- between "prevented" and "LMF".

UNITED STATES PATENT AND TRADEMARK OFFICE
CERTIFICATE OF CORRECTION

PATENT NO. : 5,348,739
DATED : September 20, 1994
INVENTOR(S) : Jan U. K. Hellstrand, et al It is certified that error appears in the above-indentified patent and that said Letters Patent is hereby corrected as shown below:

In column 10, line 60, please replace "the figure" with --Figure 1--.

In column 11, line 17, please replace the period after the word "vehicle" with a comma.

In column 11, line 36, please insert --and YAC-1-- after the first appearance of "K562" and delete the second occurrence of "K562".

In column 12, line 21, please replace "mean the" with --represent the mean--.

In column 12, line 51, please replace "augment" with --augments--.

In column 12, line 52, please replace "*in vivo*" with --*in vitro*--.

In column 12, line 57, please replace "*in vitro*" with --*in vivo*--.

In column 13, line 4, please replace the comma after "752" with a period.

In column 13, line 7, please replace "Sacnd" with --Scand-- and delete the word "roll".

In column 13, line 8, please replace the word "shogun" with the word --shown--.

In column 13, line 26, please replace the word "Hellstranc" with --Hellstrand--.

In column 13, line 27, please replace the comma after "4099" with a period.

UNITED STATES PATENT AND TRADEMARK OFFICE
CERTIFICATE OF CORRECTION

PATENT NO. : 5,348,739

DATED : September 20, 1994

INVENTOR(S) : Jan U. K. Hellstrand, et al

It is certified that error appears in the above-indentified patent and that said Letters Patent is hereby corrected as shown below:

Column 13, line 63, please replace "G6teborg" with --Göteborg--.

In column 14, line 14, please replace the word "rantidine" with --ranitidine--.

In column 14, line 23, please replace the left bracket with a left parenthesis.

In column 14, line 25, please insert a period after "U" and insert --One U-- after the period.

In column 15, line 10, please replace "I1-2" with --IL-2--.

In column 15, line 13, please replace "rIL-2" with --rIL-2--.

In column 15, line 16, please insert a semicolon after the first occurrence of the word "cells".

UNITED STATES PATENT AND TRADEMARK OFFICE
CERTIFICATE OF CORRECTION

PATENT NO. : 5,348,739

DATED : September 20, 1994

INVENTOR(S) : Jan U. K. Hellstrand, et al

It is certified that error appears in the above-indentified patent and that said Letters Patent is hereby corrected as shown below:

Columns 15-16,
In Table 3, in the title, please replace "I1-2" with --IL-2-- and please replace "b16" with --B16--.

In Table 3, second column, please replace "C57B" with --C57BL--.

In Table 3, footnote a, please replace "IL02" with --IL-2-- and please delete the apostrophe after "kg".

In Table 3, footnote b, please delete the "j" before "0.01", please replace the "c" with --<-- and please insert --<-- between the "p" and "0.05".

Column 18,
In Claim 15, at line 11, please replace "f" with --of--.

Column 18,
In Claim 15, at line 13, please replace "analoq" with --analogs--.

Signed and Sealed this

Thirty-first Day of January, 1995

Attest:

BRUCE LEHMAN

*Attesting Officer*     *Commissioner of Patents and Trademarks*